(12) United States Patent
Saruwatari

(10) Patent No.: US 10,455,173 B2
(45) Date of Patent: Oct. 22, 2019

(54) IMAGE SENSOR AND ELECTRONIC CAMERA

(71) Applicant: NIKON CORPORATION, Tokyo (JP)

(72) Inventor: Osamu Saruwatari, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/763,137

(22) PCT Filed: Sep. 27, 2016

(86) PCT No.: PCT/JP2016/078523
§ 371 (c)(1),
(2) Date: Mar. 26, 2018

(87) PCT Pub. No.: WO2017/057398
PCT Pub. Date: Apr. 6, 2017

(65) Prior Publication Data
US 2018/0278873 A1 Sep. 27, 2018

(30) Foreign Application Priority Data
Sep. 30, 2015 (JP) ................... 2015-195283

(51) Int. Cl.
*H04N 5/369* (2011.01)
*H04N 5/374* (2011.01)
(Continued)

(52) U.S. Cl.
CPC ........... *H04N 5/3698* (2013.01); *H01L 27/14* (2013.01); *H01L 27/146* (2013.01);
(Continued)

(58) Field of Classification Search
CPC .. H04N 5/3698; H04N 5/374; H04N 5/35536; H04N 5/361; H04N 5/3745; H01L 27/148; H01L 27/16421; H01L 27/14627; H01L 27/14634; H01L 27/14636; H01L 27/1464; H01L 31/00
(Continued)

(56) References Cited

U.S. PATENT DOCUMENTS 10,277,856 B2 * 4/2019 Okura ................... H04N 5/378
348/308
2005/0224841 A1 10/2005 Nakamura et al.
(Continued)

FOREIGN PATENT DOCUMENTS

JP    2006-180111 A    7/2006
JP    2007-151069 A    6/2007
(Continued)

OTHER PUBLICATIONS

Nov. 8, 2016 International Search Report issued in International Patent Application No. PCT/JP2016/078523.
(Continued)

*Primary Examiner* — Marly S Camargo
(74) *Attorney, Agent, or Firm* — Oliff PLC

(57) ABSTRACT

An image sensor includes a first voltage source that supplies a first voltage and a plurality of pixels supplied with the first voltage. The pixel includes a photoelectric conversion unit that photoelectrically converts incident light, an accumulation unit to which an electric charge resulting from photoelectric conversion by the photoelectric conversion unit is transferred and accumulated, a transfer unit that transfers the electric charge from the photoelectric conversion unit to the accumulation unit; a second voltage source that supplies a second voltage, and a supply unit that supplies the transfer unit with a transfer signal based on either the first voltage supplied by the first voltage source or the second voltage supplied by the second voltage source.

11 Claims, 7 Drawing Sheets

(51) Int. Cl.
*H04N 5/355* (2011.01)
*H01L 27/146* (2006.01)
*H01L 27/148* (2006.01)
*H01L 31/00* (2006.01)
*H01L 27/14* (2006.01)
*H04N 5/361* (2011.01)
*H04N 5/3745* (2011.01)

(52) U.S. Cl.
CPC ......... *H04N 5/35536* (2013.01); *H04N 5/361* (2013.01); *H04N 5/374* (2013.01); *H04N 5/3745* (2013.01); *H01L 27/1464* (2013.01); *H01L 27/14621* (2013.01); *H01L 27/14627* (2013.01); *H01L 27/14634* (2013.01); *H01L 27/14636* (2013.01); *H01L 27/14645* (2013.01)

(58) Field of Classification Search
USPC ......... 348/308, 294–304; 257/291, 292, 443, 257/226, 257, 462; 438/57, 67, 90, 107
See application file for complete search history.

(56) References Cited

U.S. PATENT DOCUMENTS

| | | | |
|---|---|---|---|
| 2006/0214195 A1* | 9/2006 | Kobayashi | H01L 27/14609 257/222 |
| 2007/0096238 A1 | 5/2007 | Oike et al. | |
| 2010/0141816 A1 | 6/2010 | Maruyama et al. | |
| 2011/0074993 A1 | 3/2011 | Okita et al. | |

FOREIGN PATENT DOCUMENTS

| | | | | |
|---|---|---|---|---|
| JP | 2009-0182992 A | | 8/2009 | |
| JP | 2010-225927 A | | 10/2010 | |
| JP | 2012-147004 A | | 8/2012 | |
| JP | 2013-033852 | * | 2/2013 | ............. H01L 24/14 |
| JP | 2013-033852 A | | 2/2013 | |
| WO | 2015/129197 A1 | | 9/2015 | |

OTHER PUBLICATIONS

Jul. 11, 2017 Office Action issued in Taiwanese Patent Application No. 105131636.
Jun. 19, 2018 Office Action issued in Taiwanese Patent Application No. 105131636.
Mar. 27, 2019 Office Action issued in Korean Patent Application No. 2018-7008365.
Apr. 8, 2019 Extended Search Report issued in European Patent Application No. 16851569.0.
May 21, 2019 Office Action issued in Japanese Application No. 2017-543451.
May 30, 2019 Office Action issued in Taiwanese Patent Application No. 105131636.

* cited by examiner

IMAGE SENSOR AND ELECTRONIC CAMERA

TECHNICAL FIELD

The present invention relates to an image sensor and an electronic camera.

BACKGROUND ART

Image sensors capable of controlling an exposure time for each frame are known in the art (e.g., PTL1). In order to control the exposure time for each pixel in conventional image sensors, each pixel has to be provided with a power source for supplying a negative voltage and a power source for supplying a positive voltage. This poses a problem of a reduction in an aperture ratio.

CITATION LIST

Patent Literature

PTL1: Japanese Laid-Open Patent Publication No. 2006-180111

SUMMARY OF INVENTION

An image sensor according to the 1st aspect of the present invention comprises a first voltage source that supplies a first voltage and a plurality of pixels supplied with the first voltage, wherein the pixel includes: a photoelectric conversion unit that photoelectrically converts incident light; an accumulation unit to which an electric charge resulting from photoelectric conversion by the photoelectric conversion unit is transferred and accumulated; a transfer unit that transfers the electric charge from the photoelectric conversion unit to the accumulation unit; a second voltage source that supplies a second voltage; and a supply unit that supplies the transfer unit with a transfer signal based on either the first voltage supplied by the first voltage source or the second voltage supplied by the second voltage source.

DESCRIPTION OF EMBODIMENTS

First Embodiment

Figure 1:
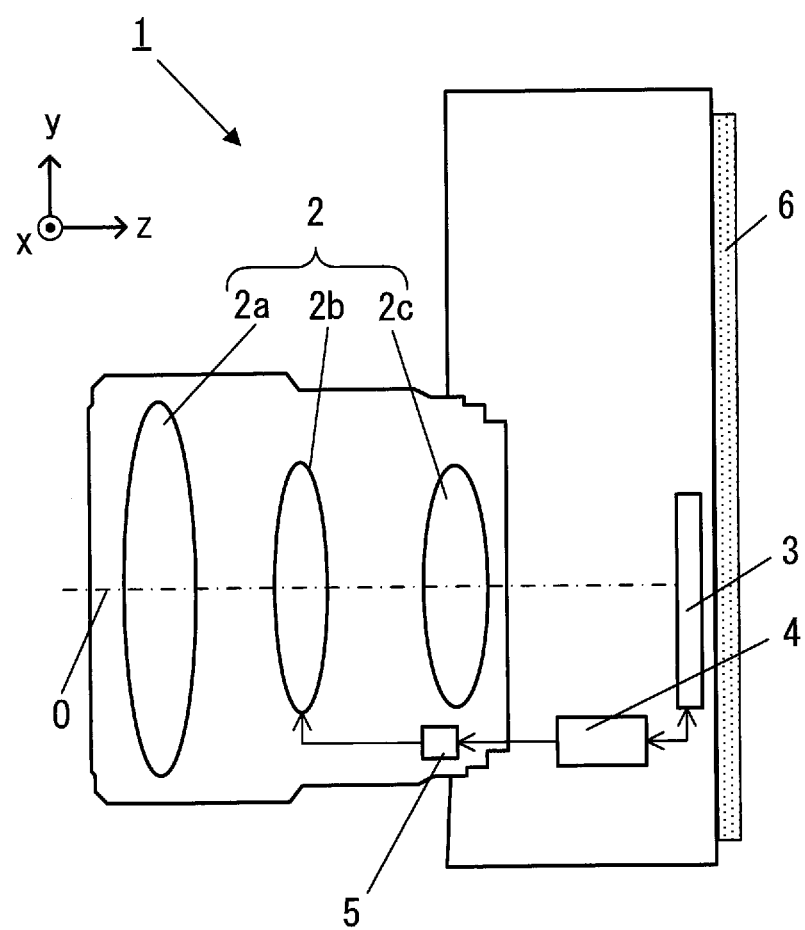
FIG. 1 is a cross-sectional view schematically illustrating a configuration of an image-capturing apparatus.

FIG. 1 is a cross-sectional view schematically illustrating a configuration of an image-capturing apparatus including an image sensor according to a first embodiment. The image-capturing apparatus 1 includes an image-capturing optical system 2, an image sensor 3, a control unit 4, a lens driving unit 5, and a display unit 6.

The image-capturing optical system 2 forms an object image on an image-capturing plane of the image sensor 3. The image-capturing optical system 2 includes a lens 2a, a focusing lens 2b, and a lens 2c. The focusing lens 2b is a lens for adjusting a focal point of the image-capturing optical system 2. The focusing lens 2b can be driven in an optical axis O direction.

The lens driving unit 5 has an actuator (not shown). Using the actuator, the lens driving unit 5 drives the focusing lens 2b in the optical axis O direction by a desired amount. The image sensor 3 captures the object image to output an image signal. The control unit 4 controls the image sensor 3 and other components. The control unit 4 performs image processing or other processing on an image signal outputted by the image sensor 3, and then records the processed image signal in a recording medium (not shown) or displays an image on the display unit 6. The display unit 6 is a display device having a display member such as a liquid crystal panel.

Figure 2:
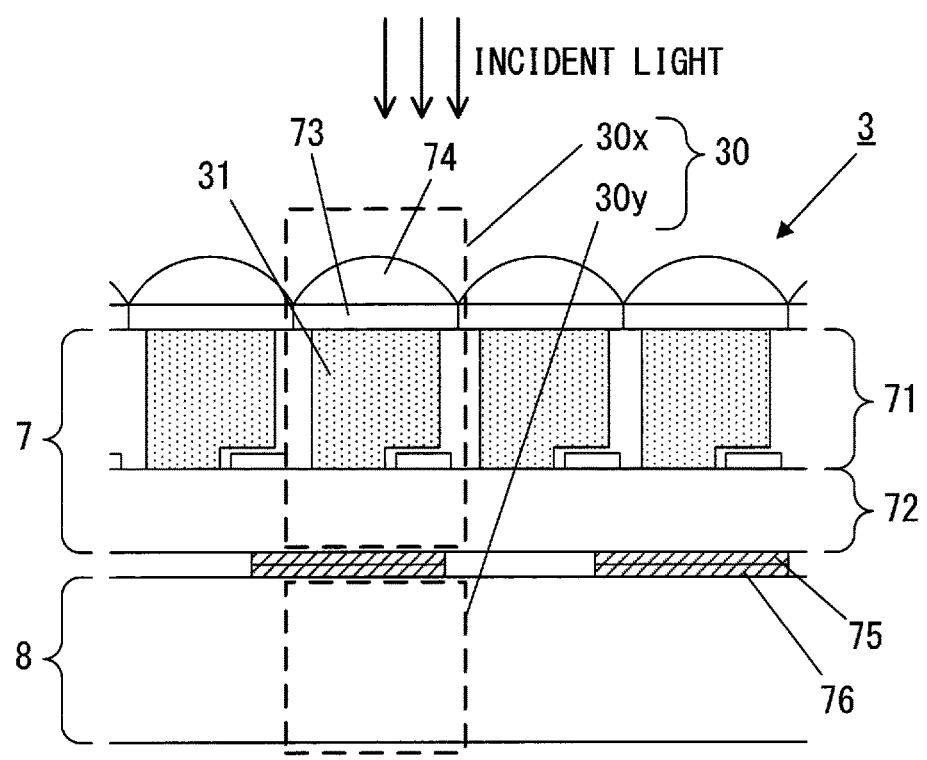
FIG. 2 is a cross-sectional view of an image sensor.

FIG. 2 is a cross-sectional view of the image sensor 3. FIG. 2 illustrates only a part of the cross section of the entire image sensor 3. The image sensor 3 is a so-called backside illumination image sensor. The image sensor 3 photoelectrically converts incident light that is incident from above in the figure. The image sensor 3 includes a first semiconductor substrate 7 and a second semiconductor substrate 8.

The first semiconductor substrate 7 includes a PD layer 71 and a wiring layer 72. The PD layer 71 is arranged on a back surface side of the wiring layer 72. A plurality of photodiodes 31, which are pinned (buried) photodiodes, are two-dimensionally arranged in the PD layer 71. A surface of the PD layer 71 on the wiring layer 72 side (i.e., a surface opposite to the incident light side) therefore has a conductivity type opposite to that of the PD layer 71. For example, if the PD layer 71 is an N-type semiconductor layer, a P-type semiconductor layer having a high concentration and a small thickness is arranged on the surface of the PD layer 71 on the wiring layer 72 side. A ground voltage (GND) is applied to the first semiconductor substrate 7 as a substrate voltage. The second semiconductor substrate 8 has a variety of circuits arranged thereon for reading signals from the photodiode 31. Specifically, an A/D conversion unit 302, a sampling unit 303, a pixel value saving unit 304, a calculation unit 305, and a part of a pixel driving unit 307 (a transfer signal supply unit 307a and a second reset signal supply unit 307c that handle a voltage Vneg described later), which will be described later, are arranged in the second semiconductor substrate 8.

The image sensor 3 includes a power supply unit 94, which is a first voltage source, for supplying each pixel 30 with the voltage Vneg, which is a first voltage. The voltage Vneg is lower than a substrate voltage of the first semiconductor substrate 7. In the present embodiment, the substrate voltage of the first semiconductor substrate 7 is the ground voltage. Accordingly, the voltage Vneg is a negative voltage lower than the ground voltage. The power supply unit 94 is not provided individually for each pixel 30, but a single common power supply unit 94 is provided for a plurality of pixels 30.

If a power supply unit that supplies each pixel 30 with the voltage Vneg lower than the substrate voltage of the first semiconductor substrate 7 is arranged individually for each pixel 30, the image sensor requires complicated circuits. This can reduce a yield of the image sensors. The image sensor 3 according to the present embodiment enables the voltage Vneg to be supplied from the outside of each pixel 30 to the pixel 30 with a simple configuration as will be described later. This eliminates the problem described above.

It should be noted that the voltage Vneg lower than the substrate voltage of the first semiconductor substrate 7 is required in order to prevent the electric charge from being transferred from the photodiode 31 to the floating diffusion FD when the transfer transistor Tx is off, as will be described later.

The power supply unit 94 for supplying the voltage Vneg is provided in the first semiconductor substrate 7 in the present embodiment. It will be noted that the power supply unit 94 may be provided at a location other than the first semiconductor substrate 7. For example, the power supply unit 94 may be provided on the second semiconductor substrate 8, and the voltage Vneg may be supplied to the first semiconductor substrate 7 via a bump to make an electrical connection with each pixel 30.

A plurality of color filters 73, each corresponding to its individual photodiode among the plurality of photodiodes 31, are provided on the light incident side in the PD layer 71. Different types of color filters 73 are available, which transmit different wavelength ranges corresponding to red (R), green (G), and blue (B), for example. Three types of color filters 73 corresponding to red (R), green (G), and blue (B), for example, are here arranged in a Bayer array.

A plurality of microlenses 74, each corresponding to its individual color filter among the plurality of color filters 73, are provided on the light incident side in the color filter 73. The microlens 74 converges the incident light toward the corresponding photodiode 31. After having passed through the microlens 74, the incident light is filtered by the color filter 73 to transmit only a part of the wavelength range of the incident light. The filtered light is then incident on the photodiode 31. The photodiode 31 photoelectrically converts the incident light to generate an electric charge.

A plurality of bumps 75 are arranged on a surface of the wiring layer 72. A plurality of bumps 76 corresponding to the plurality of bumps 75 are arranged on a surface of the second semiconductor substrate 8 facing the wiring layer 72. The plurality of bumps 75 and the plurality of bumps 76 are bonded together. The first semiconductor substrate 7 and the second semiconductor substrate 8 are electrically connected via the plurality of bumps 75 and the plurality of bumps 76.

As will be described in detail later, the image sensor 3 has a plurality of pixels 30. One pixel 30 includes a first pixel 30x provided in the first semiconductor substrate 7 and a second pixel 30y provided in the second semiconductor substrate 8. One first pixel 30x includes one microlens 74, one color filter 73, one photodiode 31, and other components. The first pixel 30x additionally includes a variety of circuits (described later) provided in the first semiconductor substrate 7, such as an individual power supply unit 341 which is a second voltage source for supplying a voltage V1 which is a second voltage. The second pixel 30y includes a variety of circuits (described later) provided in the second semiconductor substrate 8.

Figure 3:
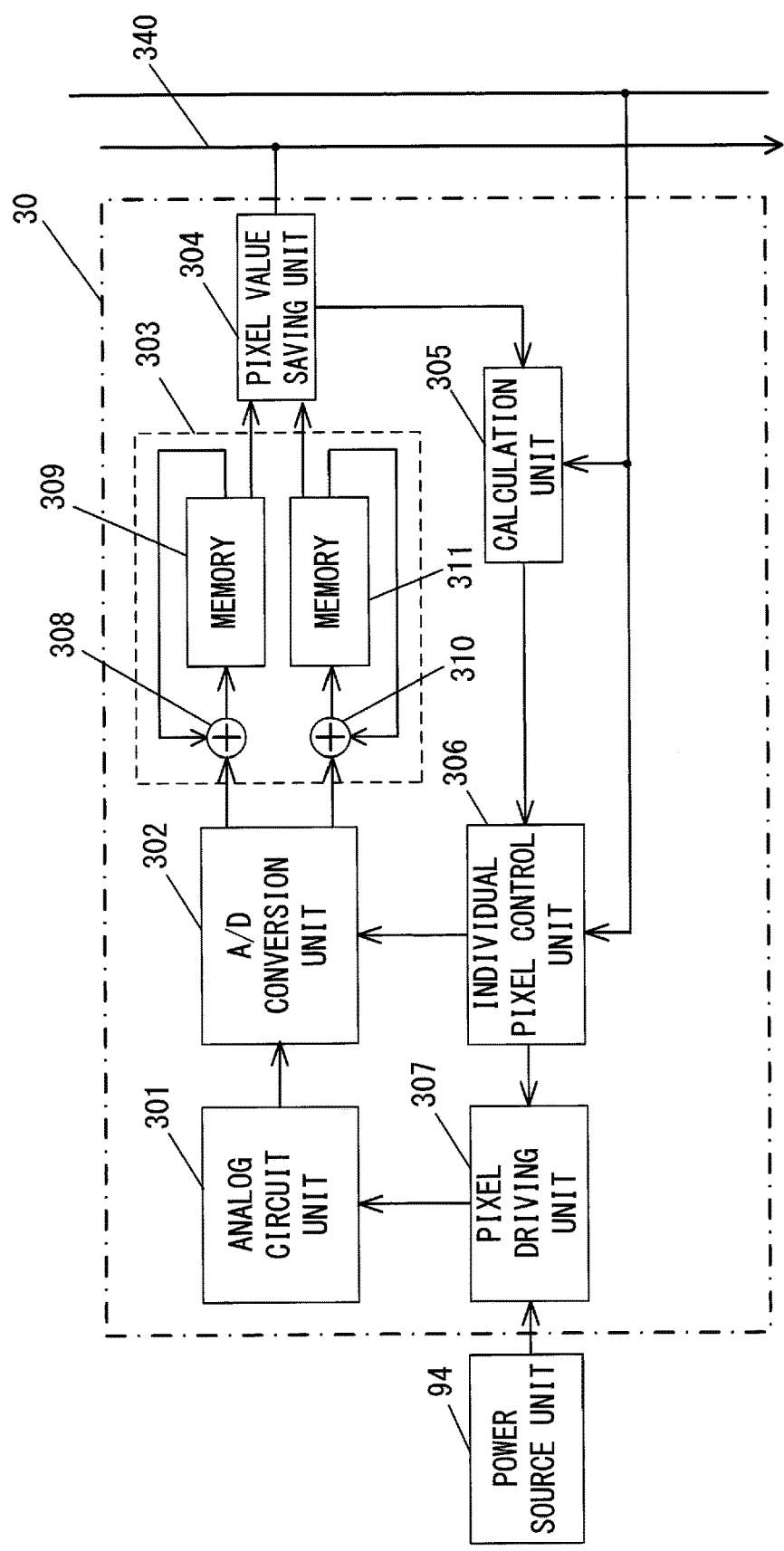
FIG. 3 is a block diagram schematically illustrating a configuration of a pixel.

FIG. 3 is a block diagram schematically illustrating a configuration of the pixel 30. The pixel 30 includes an analog circuit unit 301, an A/D conversion unit 302, a sampling unit 303, a pixel value saving unit 304, a pixel driving unit 307, an individual pixel control unit 306, and a calculation unit 305.

The analog circuit unit 301 outputs a signal resulting from the photoelectric conversion of the incident light as an analog signal to the A/D conversion unit 302. The A/D conversion unit 302 samples the analog signal outputted by the analog circuit unit 301 to output a digital signal multiplied by a predetermined gain. The A/D conversion unit 302 repeatedly samples a pixel reset signal and a pixel signal and individually outputs a sampling result of the pixel reset signal and a sampling result of the pixel signal as digital signals.

The sampling unit 303 calculates and saves an integral value of the sampling result of the pixel reset signal and the sampling result of the pixel signal. The sampling unit 303 includes a first adder 308 and a first memory 309 for the pixel reset signal, and a second adder 310 and a second memory 311 for the pixel signal.

The sampling unit 303 adds the sampling result of the pixel reset signal outputted by the A/D conversion unit 302 and the integral value of previous sampling results saved in the first memory 309, by means of the first adder 308. The sampling unit 303 stores the resulting sum in the first memory 309. The sampling unit 303 updates the value stored in the first memory 309 every time a sampling result of the pixel reset signal is outputted by the A/D conversion unit 302.

The sampling unit 303 adds the sampling result of the pixel signal outputted by the A/D conversion unit 302 and the integral value of previous sampling results saved in the second memory 311, by means of the second adder 310. The sampling unit 303 stores the resulting sum in the second memory 311. The sampling unit 303 updates the value stored in the second memory 311 every time a sampling result of the pixel signal is outputted by the A/D conversion unit 302.

In this way, the A/D conversion unit 302 repeatedly samples the pixel reset signal and the pixel signal and the sampling unit 303 executes a process of integrating the sampling results. This process is a process known as a correlated multiple sampling.

Once a predetermined number of samplings, which has been determined by the individual pixel control unit 306, has been completed, the sampling unit 303 outputs a digital value to the pixel value saving unit 304, the digital value being based on the value stored in the first memory 309 and the value stored in the second memory 311. The pixel value saving unit 304 stores the digital value as a photoelectric conversion result in the pixel 30. The pixel value saving unit 304 is connected to a signal line 340. The digital value stored in the pixel value saving unit 304 is externally readable via the signal line 340.

The calculation unit 305 calculates the number of repetitions, an exposure time, a gain, and other parameters in the correlated multiple sampling process, based on an externally determined exposure time and the last photoelectric conversion result saved in the pixel value saving unit 304. The individual pixel control unit 306 outputs the number of repetitions and the gain calculated by the calculation unit 305 to the A/D conversion unit 302. The individual pixel control unit 306 outputs the exposure time and the gain calculated by the calculation unit 305 to the pixel driving unit 307. The pixel driving unit 307 outputs a variety of drive signals (described later) to the analog circuit unit 301. The drive signals drive the elements of the analog circuit unit 301.

Figure 4:
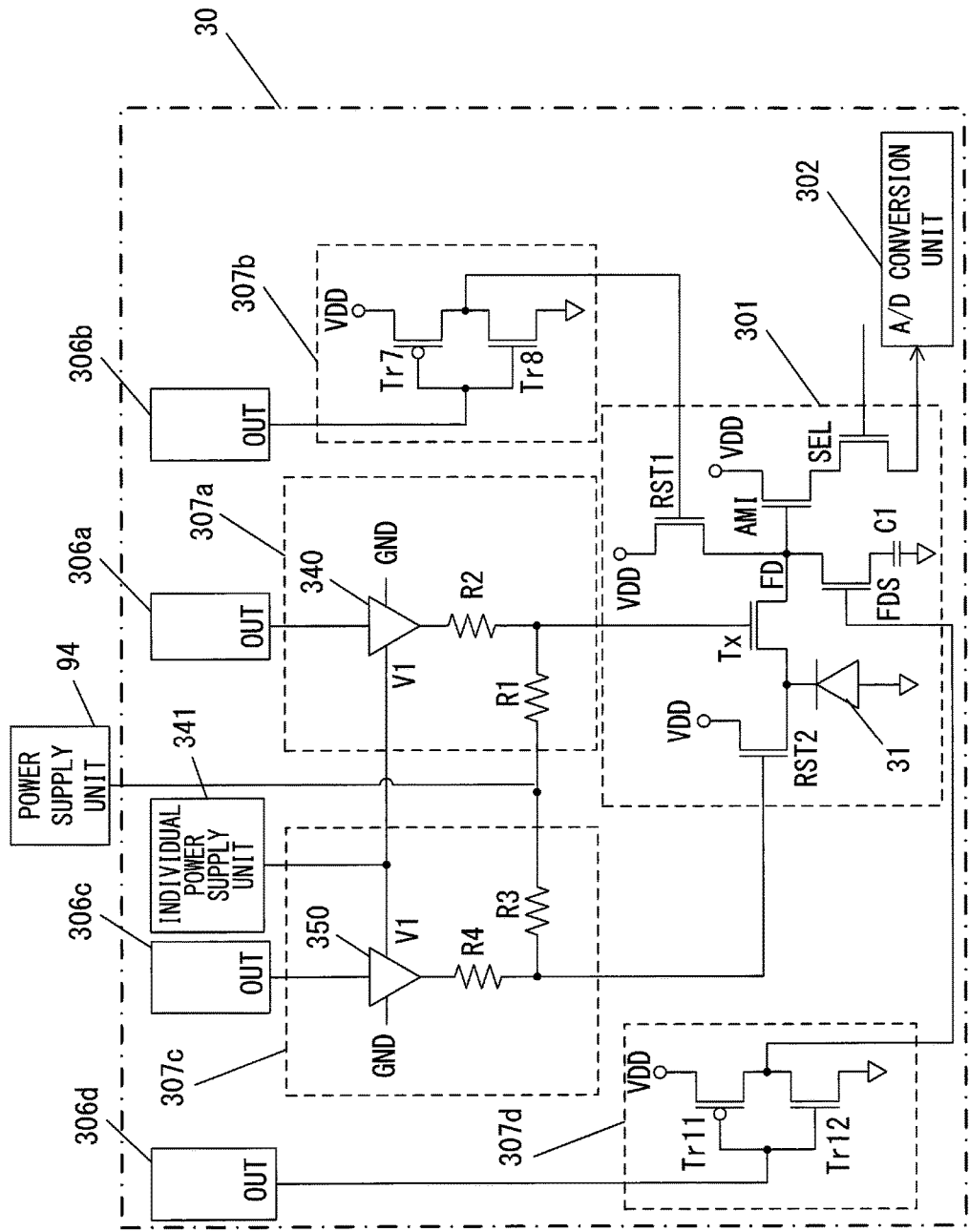
FIG. 4 is a circuit diagram of an analog circuit unit and a pixel driving unit.

FIG. 4 is a circuit diagram of the analog circuit unit 301, the individual pixel control unit 306, and the pixel driving unit 307. For the sake of convenience, FIG. 4 illustrates only parts of the individual pixel control unit 306 and the pixel driving unit 307. The parts of the individual pixel control unit 306 are designated by reference numerals 306a, 306b, and so on and the parts of the pixel driving unit 307 are designated by reference numerals 307a, 307b, and so on.

The analog circuit unit 301 includes a photodiode 31, a transfer transistor Tx, a floating diffusion FD, a first reset transistor RST1, a second reset transistor RST2, an amplification transistor AMI, a selection transistor SEL, a capacitance expansion transistor FDS, and a capacitor C1.

The photodiode 31 is a photoelectric conversion unit that photoelectrically converts incident light to generate an amount of electric charge depending on a light amount of the incident light. The transfer transistor Tx is a transfer unit that transfers the electric charge generated by the photodiode 31 to the floating diffusion FD in response to a transfer signal supplied from a transfer signal supply unit 307a (described later). The floating diffusion FD is an accumulation unit that accumulates the electric charge transferred by the transfer transistor Tx. The amplification transistor AMI outputs a signal depending on an amount of the electric charge accumulated in the floating diffusion FD. When the selection transistor SEL is on, the signal outputted by the amplification transistor AMI is inputted to the A/D conversion unit 302.

The analog circuit unit 301 includes two reset transistors: a first reset transistor RST1 and a second reset transistor RST2. When the floating diffusion FD is reset, the first reset transistor RST1 is supplied with a first reset signal from a first reset signal supply unit 307b (described later). The first reset signal supply unit 307b (described later) supplies a signal representing the voltage VDD as the first reset signal. The first reset transistor RST1 resets the floating diffusion FD in response to the first reset signal. When the photodiode 31 is reset, the second reset transistor RST2 is supplied with a second reset signal from a second reset signal supply unit 307c (described later). The second reset signal supply unit 307c (described later) supplies a signal representing the voltage VDD as the second reset signal. The second reset transistor RST2 resets the photodiode 31 in response to the second reset signal.

The capacitance expansion transistor FDS switches a connection between the floating diffusion FD and the capacitor C1 in response to a capacitance expansion signal supplied from a capacitance expansion signal supply unit 307d (described later). For example, if an incident light amount to the photodiode 31 is large and the floating diffusion FD could be saturated, the capacitance expansion transistor FDS is turned on to connect the floating diffusion FD and the capacitor C1. This substantially increases the capacitance of the floating diffusion FD by an amount equal to the capacitance of the capacitor C1. This increase allows the floating diffusion FD to handle a larger light amount.

The first reset signal supply unit 307b is a CMOS circuit including a pMOS transistor Tr7 and an nMOS transistor Tr8. Based on an output signal of a first reset control unit 306b, the first reset signal supply unit 307b supplies a gate of the first reset transistor RST1 with either the voltage VDD (a predetermined power supply voltage; the same applies hereinafter) or the voltage GND as the first reset signal. As described above, the first reset control unit 306b is a part of the individual pixel control unit 306 and the first reset signal supply unit 307b is a part of the pixel driving unit 307. It should be noted that, for an overdrive, the first reset control unit 306b supplies the gate of the first reset transistor RST1 with a voltage VRST1H higher than the voltage VDD, instead of the voltage VDD.

The capacitance expansion signal supply unit 307d is a CMOS circuit including a pMOS transistor Tr11 and an nMOS transistor Tr12. Based on an output signal of a capacitance expansion control unit 306d, the capacitance expansion signal supply unit 307d supplies a gate of the capacitance expansion transistor FDS with either the voltage VDD or the voltage GND as the capacitance expansion signal. As described above, the capacitance expansion control unit 306d is a part of the individual pixel control unit 306 and the capacitance expansion signal supply unit 307d is a part of the pixel driving unit 307.

The transfer signal supply unit 307a includes a buffer 340, a resistor R1, and a resistor R2. The buffer 340 is supplied with a transfer control signal by the transfer control unit 306a. The transfer control unit 306a outputs either a predetermined high-level voltage (e.g., the voltage VDD) or a predetermined low-level voltage (e.g., the ground voltage which is the substrate voltage of the first semiconductor substrate 7) as the transfer control signal to the buffer 340. The buffer 340 outputs the voltage V1 supplied from the individual power supply unit 341 in the pixel 30 if the transfer control signal is the high-level voltage and outputs the ground voltage which is the substrate voltage of the first semiconductor substrate 7 if the transfer control signal is the low-level voltage. The voltage V1 is higher than the substrate voltage of the first semiconductor substrate 7. In the present embodiment, the substrate voltage of the first semiconductor substrate 7 is the ground voltage. The voltage V1 is, therefore, a positive voltage higher than the ground voltage.

An output terminal of the buffer 340 is connected to a gate of the transfer transistor Tx via the resistor R2. The power supply unit 94 supplies the voltage Vneg between the resistor R2 and the transfer transistor Tx via the resistor R1. In other words, behind the gate electrode as viewed from the transfer transistor Tx, the wiring is branched into two wirings, one of which is connected to the power supply unit 94 via the resistor R1 and the other is connected to the buffer 340 via the resistor R2.

If the buffer 340 outputs the voltage V1, a voltage Vg1 determined by the following equation (1) is applied to the gate of the transfer transistor Tx. In the following equation (1), r1 is a resistance value of the resistor R1 and r2 is a resistance value of the resistor R2.

$$Vg1=(Vneg \times r2+V1 \times r1)/(r1+r2) \quad (1)$$

Assuming that Vneg is −2 V, V1 is 8 V, and r1 is equal to r2, for example, the voltage Vg1 is 3 V. In other words, when the buffer 340 outputs the voltage V1, a positive voltage of 3 V is applied to the gate of the transfer transistor Tx so that the transfer transistor Tx is in its on state. In other words, if the transfer control signal is the high-level voltage, the transfer transistor Tx transfers an electric charge generated by the photodiode 31 to the floating diffusion FD.

On the other hand, if the buffer 340 outputs the ground voltage, a voltage Vg2 determined by the following equation (2) is applied to the gate of the transfer transistor Tx.

$$Vg2=(Vneg \times r2)/(r1+r2) \quad (2)$$

Assuming that Vneg is −2 V and r1 is equal to r2, for example, the voltage Vg2 is −1 V. In other words, when the buffer 340 outputs the ground voltage which is the substrate voltage of the first semiconductor substrate 7, a negative voltage of −1 V lower than the substrate voltage of the first semiconductor substrate 7 is applied to the gate of the transfer transistor Tx so that the transfer transistor Tx is in its off state. In other words, if the transfer control signal is the low-level voltage, the transfer transistor Tx does not transfer an electric charge generated by the photodiode 31 to the floating diffusion FD.

The transfer signal supply unit 307a configured in the above-described manner supplies the gate of the transfer transistor Tx with either a positive voltage or a voltage (a negative voltage in this embodiment) lower than the substrate voltage of the first semiconductor substrate 7, as the transfer signal, based on the output signal of the transfer control unit 306a. As described above, the transfer control unit 306a is a part of the individual pixel control unit 306 and the transfer signal supply unit 307a is a part of the pixel driving unit 307. It should be noted that the voltage lower than the substrate voltage of the first semiconductor substrate 7 is applied to the gate of the transfer transistor Tx in order to prevent the electric charge from being transferred from the photodiode 31 to the floating diffusion FD when the transfer transistor Tx is off.

The second reset signal supply unit 307c includes a buffer 350, a resistor R3, and a resistor R4. The second reset signal supply unit 307c supplies the gate of the second reset transistor RST2 with either a positive voltage or a voltage (a negative voltage in this embodiment) lower than the substrate voltage of the first semiconductor substrate 7, as the second reset signal, based on the output signal of the second reset control unit 306c. The configuration of the second reset signal supply unit 307c is the same as that of the transfer signal supply unit 307a and description thereof will thus be omitted. As described above, the second reset control unit 306c is a part of the individual pixel control unit 306 and the second reset signal supply unit 307c is a part of the pixel driving unit 307.

A layout of each elements illustrated in FIGS. 3 and 4 on a semiconductor substrate will now be described. Among the units illustrated in FIGS. 3 and 4, the analog circuit unit 301, the transfer driving unit 307a, and the individual power supply unit 341 (FIG. 4) are arranged in the first semiconductor substrate 7. Other units among the units illustrated in FIGS. 3 and 4 are arranged in the second semiconductor substrate 8.

In this way, the photodiode 31 can be as large as possible. The present embodiment can achieve an increase in area of the photodiode 31, an increase in utilization efficiency of the incident light, and an improvement in saturation capacity (maximum numbers of electrons per pixel), since elements constituting the pixel 30 are arranged in the second semiconductor substrate 8 wherever possible.

Figure 5:
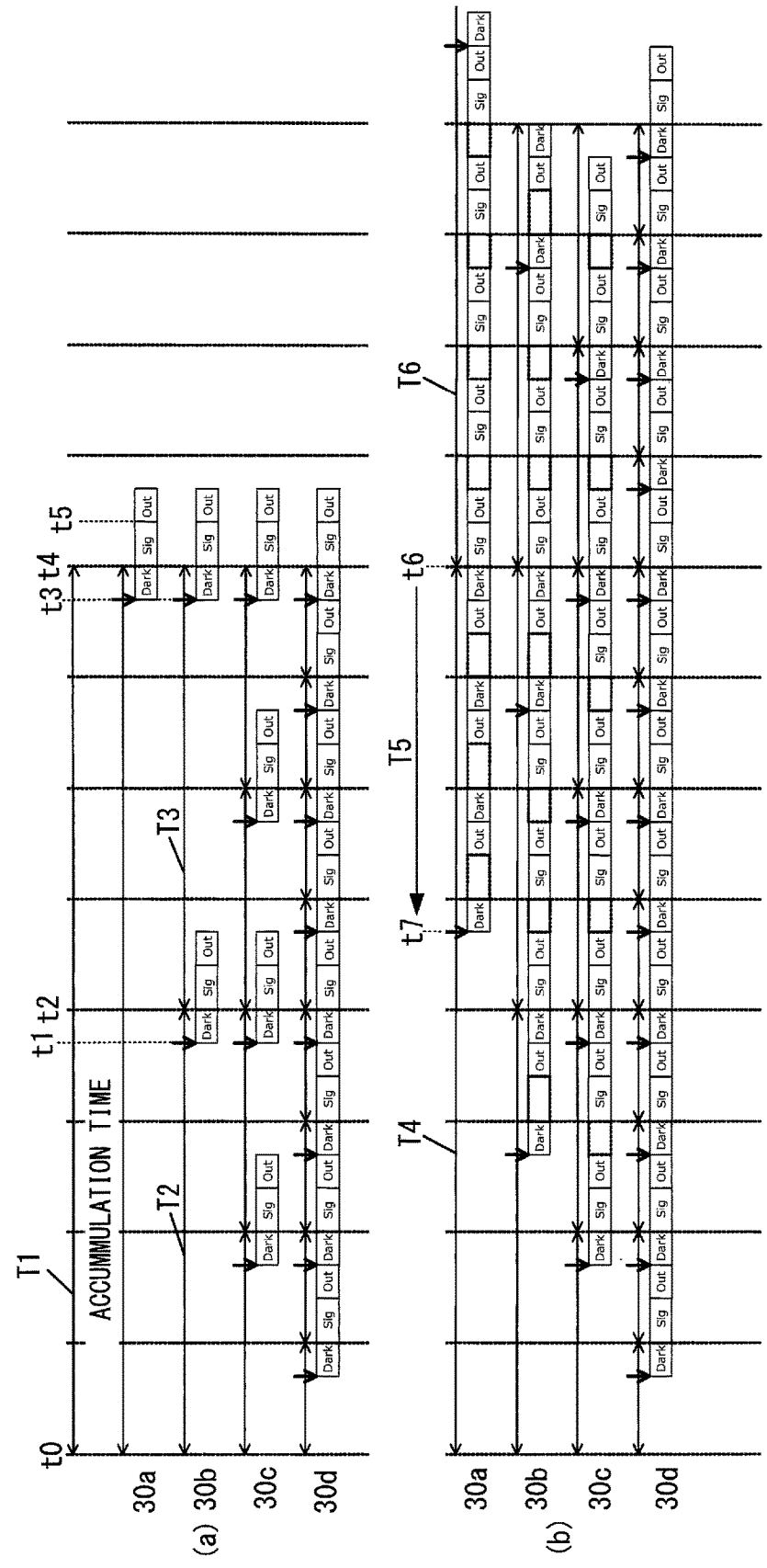
FIG. 5 is a timing chart illustrating an image-capturing sequence using the image sensor.

FIG. 5 is a timing chart illustrating an image-capturing sequence using the image sensor 3. The image sensor 3 can selectively perform multiple exposure and the correlated multiple sampling. First, a multiple exposure control will be described with reference to FIG. 5(a).

FIG. 5(a) is a timing chart in the multiple exposure for each pixel 30. The horizontal axis in FIG. 5(a) denotes time, and time proceeds to right. Rectangles marked as "Dark" in FIG. 5(a) indicate timings at which the A/D conversion unit 302 samples the pixel reset signals. Rectangles marked as "Sig" in FIG. 5(a) indicate timings at which the A/D conversion unit 302 samples the pixel signals. Rectangles marked as "Out" in FIG. 5(a) indicate timings at which the pixel value saving unit 304 outputs the digital value (the photoelectric conversion result) stored therein to peripheral circuits via the signal line 340. In FIG. 5(a), in performing the multiple exposure, the pixels 30 are classified into four pixels 30a to 30d depending on an amount of the incident light.

An operation of resetting the photodiode 31 and the floating diffusion FD at a start time t0 of an exposure period T1 is the same for all pixels 30. In the pixel 30a that receives an extremely small amount of incident light, the floating diffusion FD is then reset at a time t3 to sample the pixel reset signal. The time t3 is a time obtained by subtracting a time required for resetting the floating diffusion FD and sampling the pixel reset signal from an end time t4 of the exposure period T1. At the end time t4 of the exposure period T1, the electric charge that has been generated in a period from the time t0 to the time t4 and accumulated in the photodiode 31 is transferred to the floating diffusion FD to sample the pixel signal. Then, at a time t5, the photoelectric conversion result is stored in the pixel value saving unit 304.

In the pixel 30b that receives a slightly small amount of incident light, the externally determined exposure period T1 is equally divided into two periods T2 and T3 to perform the above-described operation twice. Specifically, at the times t1 and t3, the floating diffusion FD is reset to sample the pixel reset signal. The time t1 is a time obtained by subtracting a time required for resetting the floating diffusion FD and sampling the pixel reset signal from an end time t2 of the period T2. Then, at the time t2, the electric charge accumulated in the photodiode 31 is transferred to the floating diffusion FD to sample the pixel signal. The operation during a period from the time 3 to the time t5 is the same as in the case of the pixel 30a.

In the pixel 30c that receives a slightly large amount of incident light, the externally determined exposure period T1 is equally divided into four periods to perform the above-described operation four times. In the pixel 30d that receives an extremely large amount of incident light, the externally determined exposure period T1 is equally divided into eight periods to perform the above-described operation eight times.

In this way, the multiple exposure control enables the exposure time to individually vary for the pixels 30 receiving a large amount of incident light and the pixels 30 receiving a small amount of incident light in order to capture an image. Subdividing the exposure time and repeating the image-capturing allow a dynamic range to be extended, even if the incident light amount is so large that the floating diffusion FD would be saturated in a common image-capturing.

Next, the correlated multiplex sampling control will be described with reference to FIG. 5(b). FIG. 5(b) is a timing chart in the correlation multiple sampling control for each pixel 30. The horizontal axis in FIG. 5(b) denotes time, and time proceeds to right. Rectangles marked as "Dark" in FIG. 5(b) indicate timings at which the A/D conversion unit 302 samples the pixel reset signals. Rectangles marked as "Sig" in FIG. 5(b) indicate timings at which the A/D conversion unit 302 samples the pixel signals. Rectangles marked as "Out" in FIG. 5(b) indicate timings at which the A/D conversion unit 302 outputs the sampling results to the sampling unit 303. In FIG. 5(b), in performing the correlation multiple sampling, the pixels 30 are classified into four pixels 30a to 30d depending on an amount of the incident light.

The pixel 30a has the longest exposure time and the pixel 30d has the shortest exposure time. In the correlated multiple sampling control, the floating diffusion FD is reset at an earlier time as the pixel 30 has a longer exposure time. It thus takes a longer time until the pixel signal is sampled after resetting the floating diffusion FD, as the pixel 30 has a longer exposure time. During that period, the pixel reset signal is repeatedly sampled.

For example, in FIG. 5(b), the pixel 30a has the longest exposure time. The floating diffusion FD is reset at a time t7 that is earlier than an end time t6 of an exposure time T4 of the pixel 30a by a period T5. As a result, the pixel reset signal is sampled four times before the time t6. The pixel signal is then repeatedly sampled during a period from the end of the exposure time T4 to the end of the next exposure time T6.

A long exposure time translates into a small amount of the incident light and thus a large influence of noises on the pixel signal caused by the amplification transistor AMI, the selection transistor SEL, and the A/D conversion unit 302. In other words, the number of samplings of the pixel reset signal and the pixel signal to be performed is larger for the pixel 30 influenced to a greater extent by the noises described above. This enables a more sensitive image-capturing to be performed.

The image sensor 3 performs the above-described operations on all the pixels 30 in parallel. In other words, the pixels 30 perform in parallel the operations from the photoelectric conversion in the photodiode 31 to the storage of the digital value into the pixel value saving unit 304. The image-capturing results are sequentially read out from the pixel value saving unit 304 from one pixel 30 to another.

In this way, the image sensor 3 in the present embodiment can control the exposure time for each pixel. In order to control the exposure time for each pixel, the timing of turning on and off the transfer transistor Tx must be controlled for each pixel. In other words, the voltage (in the present embodiment, the voltage Vg1 and the voltage Vg2 which are based on the voltage V1 and the voltage Vneg) to be supplied to the gate of the transfer transistor Tx must be controlled for each pixel. Accordingly, the first power supply unit for supplying the voltage Vneg and the second power supply unit for supplying the voltage V1 must be provided for each pixel. Since the voltage handled by the first semiconductor substrate 7 is different from the voltage Vneg and the voltage V1, the first power source unit and the second power source unit would occupy a large area if they would be provided in the pixel 30. The first power supply unit particularly requires a triple well structure to avoid a forward bias with respect to the substrate, since the first power supply unit handles the voltage Vneg lower than the substrate voltage. The first power supply unit therefore requires a particularly large area. As a result, an area occupied by the photodiode 31 in the pixel 30 would be substantially reduced. This causes a substantially reduced fill factor (aperture ratio) of the photodiode 31, which can make miniaturization of the image sensor difficult. In the present embodiment, providing the power supply unit 94 which is the first power supply unit outside of the pixel as a common power supply for all pixels allows the exposure time to be controlled for each pixel, without providing the first power supply unit and the second power supply unit in the vicinity of the photodiode 31 of the first semiconductor substrate 7, i.e., without reducing the fill factor of the photodiode 31. Further, the image sensor can be reduced in size.

According to the above-described embodiment, the following operational advantages can be obtained.

(1) The image sensor 3 includes the power supply unit 94 that supplies a negative voltage, and the plurality of pixels 30. Each of the plurality of pixels 30 includes: the photodiode 31 that photoelectrically converts incident light; the floating diffusion FD that accumulates an electric charge resulting from the photoelectric conversion by the photodiode 31; the transfer transistor Tx that transfers the electric charge resulting from the photoelectric conversion by the photodiode 31 to the floating diffusion FD in response to a transfer signal; the individual power supply unit 341 that supplies a positive voltage; and the transfer signal supply unit 307a that supplies the transfer transistor Tx with either the first voltage lower than the ground voltage or the second voltage higher than the ground voltage as the transfer signal, depending on the negative voltage supplied by the power supply unit 94 and the positive voltage supplied by the individual power supply unit 341. In this way, parallel reading for the pixels can be performed without providing an individual power supply for supplying each pixel 30 with a negative voltage.

(2) The first semiconductor substrate 7 is provided with the photodiode 31, the transfer transistor Tx, the floating diffusion FD, the transfer signal supply unit 307a, and the individual power supply unit 341. The second semiconductor substrate 8 is provided with the A/D conversion unit 302 and the sampling unit 303. In this way, since the circuits handling a negative power supply are provided in the second semiconductor substrate 8 and are not provided in the first semiconductor substrate 7, there is no need to provide a diffusion layer or another layer for handling the negative power supply in the first semiconductor substrate 7. The fill factor of the photodiode 31 can thus be increased.

(3) The transfer control signal including the ground voltage and the positive voltage is inputted to the transfer signal supply unit 307a. The transfer signal supply unit 307a converts the transfer control signal into a transfer signal including a negative voltage and a positive voltage and outputs the transfer signal. In this way, the transfer signal including a negative voltage can be supplied without introducing a special circuit element for handling a negative voltage.

(4) Each of the plurality of pixels 30 includes a resistor R1 having one end connected to the power supply unit 94 and the other end connected to the transfer transistor Tx, a resistor R2 having one end from which the transfer signal is inputted and the other end connected to the transfer transistor Tx. In this way, the magnitude of the voltage supplied to the transfer transistor Tx can be easily controlled by a potential dividing circuit depending on a combination of the resistance values of the resistors R1 and R2.

Second Embodiment

Unlike the image sensor 3 according to the first embodiment, an image sensor 3 according to a second embodiment includes only one single semiconductor substrate 70, without including a second semiconductor substrate 8. The following description refers to the image sensor 3 according to the second embodiment and mainly differences from the image sensor 3 according to the first embodiment. The same components as those of the first embodiment are designated by the same reference numerals and description thereof will be omitted herein.

Figure 6:
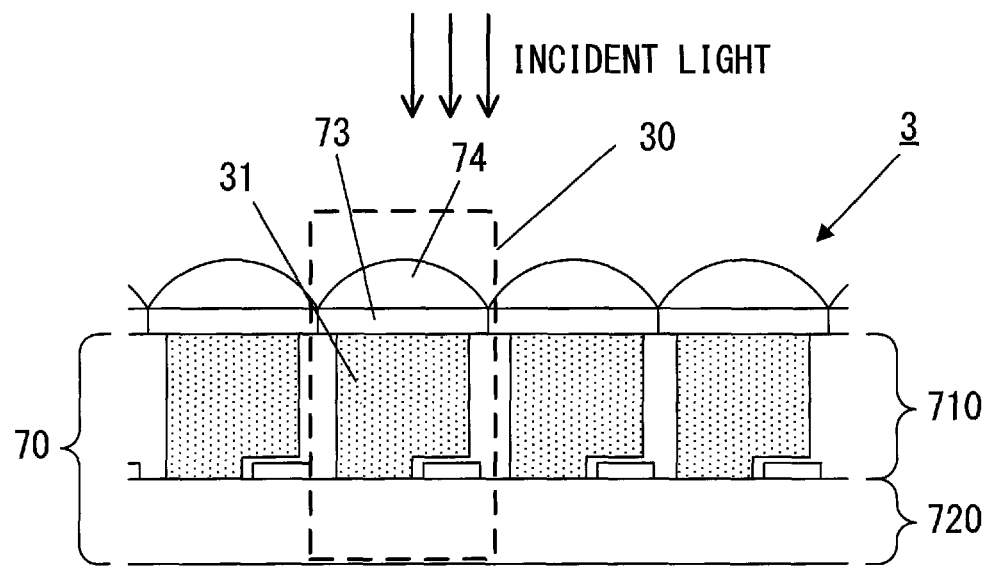
FIG. 6 is a cross-sectional view of the image sensor.

FIG. 6 is a cross-sectional view of the image sensor 3. FIG. 6 illustrates only a part of the cross section of the entire image sensor 3. The image sensor 3 is a so-called backside illumination image sensor. The image sensor 3 photoelectrically converts incident light that is incident from above in the figure.

The image sensor 3 has a plurality of pixels 30. One pixel 30 includes a microlens 74 and a color filter 73 illustrated in FIG. 6. The pixel 30 additionally includes the analog circuit unit 301, the A/D conversion unit 302, the sampling unit 303, the pixel value saving unit 304, the calculation unit 305, the individual pixel control unit 306, and the pixel driving unit 307, which are illustrated in FIG. 4. These regions are provided in a region 710. Incidentally, reference numeral 720 designates a wiring layer.

Figure 7:
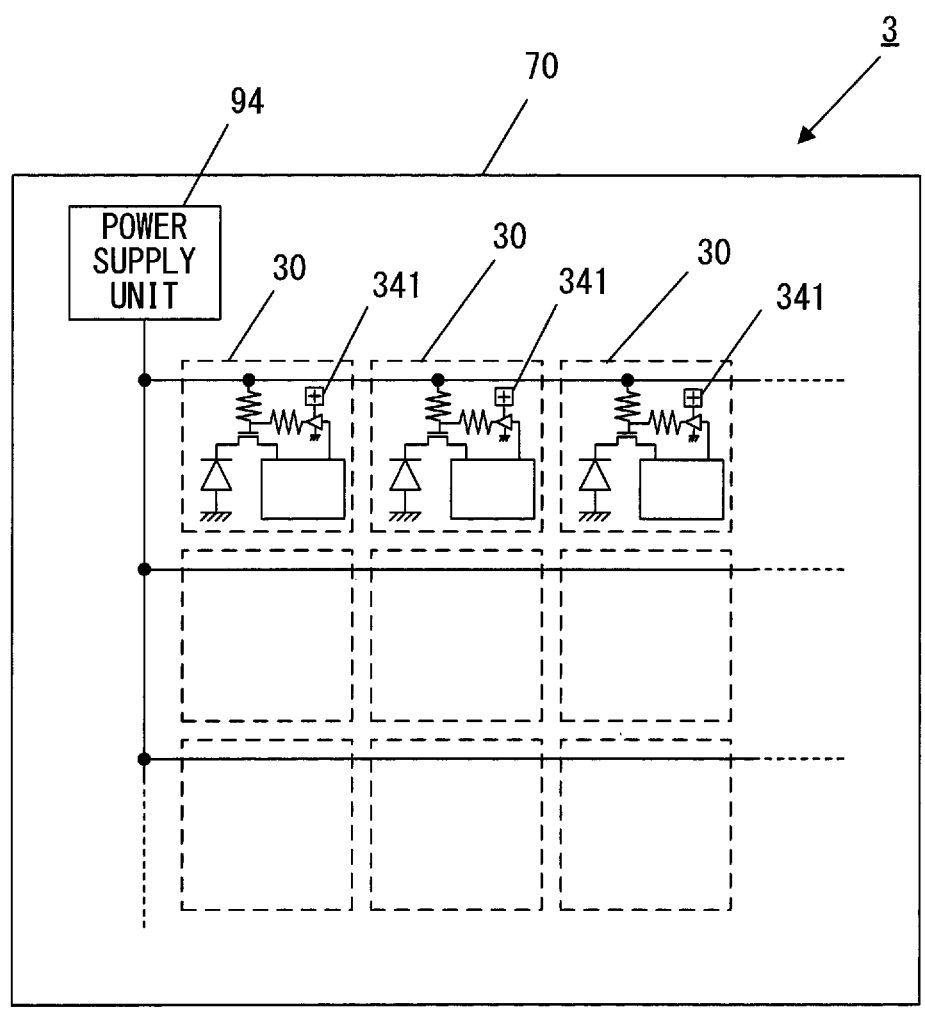
FIG. 7 is a block diagram schematically illustrating a configuration of the image sensor.

FIG. 7 is a block diagram schematically illustrating a configuration of the image sensor 3. The semiconductor substrate 70 is provided with a plurality of pixels 30 arranged in a two-dimensional array. It should be noted that FIG. 7 illustrates only a total of nine pixels 30 in 3 rows and 3 columns among the plurality of pixels 30 provided on the semiconductor substrate 70.

The semiconductor substrate 70 includes a power supply unit 94, which is a first voltage source, for supplying each pixel 30 with the voltage Vneg, which is a first voltage. The voltage Vneg is lower than the substrate voltage of the first semiconductor substrate 7. In the present embodiment, the substrate voltage of the first semiconductor substrate 7 is the ground voltage. The voltage Vneg is therefore a negative voltage lower than the ground voltage. The power supply unit 94 is not provided individually for each pixel 30, but a single common power supply unit 94 is provided for a plurality of pixels 30.

Each of the plurality of pixels 30 includes an individual power supply unit 341 that supplies a predetermined voltage V1. The individual power supply unit 341 is provided for each pixel 30. The voltage V1 supplied by the individual power supply unit 341 is higher than the substrate voltage of the first semiconductor substrate 7. In the present embodiment, the substrate voltage of the first semiconductor substrate 7 is the ground voltage. The voltage V1 is, therefore, a positive voltage higher than the ground voltage.

According to the above-described embodiment, the following operational advantages can further be obtained, in addition to the operational advantage described in the first embodiment.

(5) All elements constituting the pixel 30 are provided on the single semiconductor substrate 70. This can reduce the manufacturing cost of the image sensor 3. Additionally, a step of stacking a plurality of semiconductor substrates can be omitted, which can simplify the manufacturing process.

The following variations are also contemplated within the scope of the present invention, and one or more variations may be combined with the above embodiments.

First Variation

A switch for turning on and off an electrical connection between the power supply unit 94 and the plurality of pixels 30 may be provided between the power supply unit 94 and the plurality of pixels 30. When the switch is turned off, an electric current flowing from the plurality of pixels 30 toward the power supply unit 94 is interrupted. Providing the switch prevents the electric current from flowing between the power supply unit 94 and the transfer signal supply unit 307a when no image-capturing operation is performed. This can reduce power consumption. It should be noted that only one switch is provided upstream of the power supply unit 94 as long as the electrical connection with the power supply unit 94 is turned on and off at the same timing for all the pixels 30. Additionally, the power supply unit 94 may integrate the above-described switch therein.

Second Variation

In each of the embodiments described above, a capacitor, a coil, or other elements may be arranged instead of the resistor R1. The signal outputted from the buffer 340 is a signal having a constant frequency, and a potential dividing circuit can be configured by combining optional impedances such as capacitors and coils.

Third Variation

In the first embodiment, the resistor R1 may be a TSV (through silicon via) connecting the first semiconductor substrate 7 and the second semiconductor substrate. This facilitates to set the resistance value of the resistor R1 to a desired value.

While various embodiments and variations have been described above, the present invention is not limited to these. Other aspects contemplated within the technical idea of the present invention are also included within the scope of the present invention.

The above embodiments and variations also include the following image-capturing apparatus and electronic camera.

(1) In an image sensor including a first voltage source that supplies a first voltage and a plurality of pixels supplied with the first voltage, the pixel includes: a photoelectric conversion unit that photoelectrically converts incident light; an accumulation unit to which an electric charge resulting from the photoelectric conversion by the photoelectric conversion unit is transferred and accumulated; a transfer unit that transfers the electric charge from the photoelectric conversion unit to the accumulation unit; a second voltage source that supplies a second voltage; and a supply unit that supplies the transfer unit with a transfer signal based on either the first voltage supplied by the first voltage source or the second voltage supplied by the second voltage source.

(2) In the image sensor as recited in (1), the supply unit includes a first resistor arranged between the first voltage source and the transfer unit and a second resistor arranged between the second voltage source and the transfer unit.

(3) In the image sensor as recited in (2), a substrate voltage is applied to the image sensor, the first voltage source supplies a voltage lower than the substrate voltage, and the second voltage source supplies a voltage higher than the substrate voltage.

(4) In the image sensor as recited in (3), the transfer unit electrically connects the photoelectric conversion unit and the accumulation unit to transfer the electric charge generated by the photoelectric conversion unit to the accumulation unit, and the supply unit supplies the transfer unit with a transfer signal for electrically connecting or disconnecting the photoelectric conversion unit and the accumulation unit.

(5) The image sensor as recited in (3) or (4) includes a first semiconductor substrate provided with the plurality of pixels and a second semiconductor substrate provided with an A/D conversion unit for each of the plurality of pixels, the A/D conversion unit outputting a digital signal depending on the amount of the electric charge accumulated in the accumulation unit.

(6) In the image sensor as recited in (5), the first voltage source is provided on the second semiconductor substrate, and the first resistor includes at least an electrode connecting the first semiconductor substrate and the second semiconductor substrate.

(7) In the image sensor as recited in (3) to (5), the supply unit includes a capacitor arranged between the first voltage source and the transfer unit.

(8) In the image sensor as recited in (3) to (7), some of the plurality of supply units transfer the electric charge generated by the photoelectric conversion unit during a first period to the accumulation unit and others of the plurality of supply units transfer the electric charge generated by the photoelectric conversion unit during a second period to the accumulation unit, the second period having a length different from that of the first period.

(9) In the image sensor as recited in (3) to (8), the photoelectric conversion unit is a pinned photodiode, the transfer unit transfers the electric charge resulting from the photoelectric conversion by the photoelectric conversion unit to the accumulation unit if the transfer signal is the first voltage based on the voltage supplied by the first voltage source, and does not transfer the electric charge resulting from the photoelectric conversion by the photoelectric conversion unit to the accumulation unit if the transfer signal is the second voltage based on the voltage supplied by the first voltage source.

(10) In the image sensor as recited in (3) to (9), either a third voltage higher than or equal to the substrate voltage or a fourth voltage higher than or equal to the substrate voltage and higher than the third voltage is inputted to the supply unit; and the supply unit outputs the transfer signal that is the first voltage if the third voltage is inputted and supplies the transfer signal that is the second voltage if the fourth voltage is inputted.

(11) In the image sensor as recited in (1) to (10), each of the plurality of pixels has a switching unit that electrically connect or disconnect the supply unit and the first voltage source.

(12) An electronic camera including the image sensor as recited in (1) to (11).

The above embodiments and variations also include the following image sensor.

(1) An image sensor including a negative voltage power source unit that supplies a negative voltage and a plurality of pixels, each including: a photoelectric conversion unit that photoelectrically converts incident light; an accumulation unit that accumulates an electric charge resulting from the photoelectric conversion by the photoelectric conversion unit; a transfer unit that transfers the electric charge resulting from the photoelectric conversion by the photoelectric conversion unit to the accumulation unit; a positive voltage power source unit that supplies a positive voltage; and a transfer signal supply unit that supplies the transfer unit with either a first voltage lower than a ground voltage or a second voltage higher than the ground voltage as the transfer signal depending on the negative voltage supplied by the negative voltage power source unit and the positive voltage supplied by the positive voltage power source unit.

(2) The image sensor as recited in (1) includes a first semiconductor substrate provided with the plurality of pixels, and a second semiconductor substrate provided with an A/D conversion unit for each of the plurality of pixels, the A/D conversion unit outputting a digital signal depending on the amount of the electric charge accumulated in the accumulation unit.

(3) In the image sensor as recited in (2), the transfer signal supply unit includes a first resistor having one end connected to the negative voltage power source unit and the other end connected to the transfer unit, and a second resistor having one end from which the transfer signal is inputted and the other end connected to the transfer unit.

(4) In the image sensor as recited in (3), the negative voltage power source unit is provided in the second semiconductor substrate and the first resistor includes at least an electrode connecting the first semiconductor substrate and the second semiconductor substrate.

(5) In the image sensor as recited in (1) or (2), the transfer signal supply unit includes a capacitor having one end connected to the negative voltage power source unit and the other end connected to the transfer unit.

(6) In the image sensor as recited in (1) to (5), some of the plurality of transfer signal supply units transfer the electric charge generated by the photoelectric conversion unit during a first period to the accumulation unit and others of the plurality of transfer signal supply units transfer the electric charge generated by the photoelectric conversion unit during a second period to the accumulation unit, the second period having a length different from that of the first period.

(7) In the image sensor as recited in (1) to (6), the photoelectric conversion unit is a pinned photodiode, the transfer unit transfers the electric charge resulting from the photoelectric conversion by the photoelectric conversion unit to the accumulation unit if the transfer signal is the first voltage, and does not transfer the electric charge resulting from the photoelectric conversion by the photoelectric conversion unit to the accumulation unit if the transfer signal is the second voltage.

(8) In the image sensor as recited in (1) to (7), either a third voltage higher than or equal to the ground voltage or a fourth voltage higher than or equal to the ground voltage and higher than the third voltage is inputted to the supply unit as a drive signal, and the transfer signal supply unit outputs the transfer signal that is the first voltage if the drive signal is the third voltage and outputs the transfer signal that is the second voltage if the drive signal is the fourth voltage.

(9) In the image sensor as recited in (1) to (8), each of the plurality of pixels has a switching unit that electrically connect or disconnect the transfer signal supply unit and the negative voltage power source.

The disclosure of the following priority application is herein incorporated by reference:

Japanese Patent Application No. 2015-195283 (filed Sep. 30, 2015)

REFERENCE SIGNS LIST

3 . . . image sensor, 7 . . . first semiconductor substrate, 8 . . . second semiconductor substrate, 30 . . . pixel, 31 . . . photodiode, 70 . . . semiconductor substrate, 301 . . . analog circuit unit, 302 . . . A/D conversion unit, 303 . . . sampling unit, 306 . . . individual pixel control unit, 307 . . . pixel driving unit

The invention claimed is:

1. An image sensor, comprising
a first voltage source that supplies a first voltage and
a plurality of pixels supplied with the first voltage, wherein
the pixels each include:
a photoelectric conversion unit that photoelectrically converts incident light;
an accumulation unit to which an electric charge resulting from photoelectric conversion by the photoelectric conversion unit is transferred and accumulated;
a transfer unit that transfers the electric charge from the photoelectric conversion unit to the accumulation unit;
a second voltage source that supplies a second voltage; and
a supply unit that supplies the transfer unit with a transfer signal based on either the first voltage supplied by the first voltage source or the second voltage supplied by the second voltage source; and
the supply unit includes a capacitor arranged between the first voltage source and the transfer unit, and a second resistor arranged between the second voltage source and the transfer unit.

2. The image sensor according to claim 1, wherein:
the supply unit includes a first resistor arranged between the first voltage source and the transfer unit and a second resistor arranged between the second voltage source and the transfer unit.

3. The image sensor according to claim 2, comprising:
a first semiconductor substrate provided with the plurality of pixels; and
a second semiconductor substrate provided with an A/D conversion unit for each of the plurality of pixels, the A/D conversion unit outputting a digital signal depending on the amount of the electric charge accumulated in the accumulation unit, wherein:
the first voltage source is provided on the second semiconductor substrate; and
the first resistor includes at least an electrode connecting the first semiconductor substrate and the second semiconductor substrate.

4. The image sensor according to claim 1, wherein:
a substrate voltage is applied to the image sensor;
the first voltage source supplies a voltage lower than the substrate voltage; and
the second voltage source supplies a voltage higher than the substrate voltage.

5. The image sensor according to claim 4, wherein:
either a third voltage higher than or equal to the substrate voltage or a fourth voltage higher than or equal to the substrate voltage and higher than the third voltage is inputted to the supply unit; and
the supply unit outputs the transfer signal that is the first voltage if the third voltage is inputted and supplies the transfer signal that is the second voltage if the fourth voltage is inputted.

6. The image sensor according to claim 1, wherein:
the transfer unit electrically connects the photoelectric conversion unit and the accumulation unit to transfer the electric charge generated by the photoelectric conversion unit to the accumulation unit; and
the supply unit supplies the transfer unit with the transfer signal for electrically connecting or disconnecting the photoelectric conversion unit and the accumulation unit.

7. The image sensor according to claim 1, comprising:
a first semiconductor substrate provided with the plurality of pixels; and
a second semiconductor substrate provided with an A/D conversion unit for each of the plurality of pixels, the A/D conversion unit outputting a digital signal depending on the amount of the electric charge accumulated in the accumulation unit.

8. The image sensor according to claim 1, wherein:
a part of a plurality of supply units each corresponds to the supply unit transfer the electric charge generated by the photoelectric conversion unit during a first period to the accumulation unit and another part of the plurality of supply units transfer the electric charge generated by the photoelectric conversion unit during a second period to the accumulation unit, the second period having a length different from that of the first period.

9. The image sensor according to claim 1, wherein:
the photoelectric conversion unit is a pinned photodiode; and
the transfer unit transfers the electric charge resulting from photoelectric conversion by the photoelectric conversion unit to the accumulation unit if the transfer signal is the first voltage based on a voltage supplied by the first voltage source, and does not transfer the electric charge resulting from photoelectric conversion by the photoelectric conversion unit to the accumulation unit if the transfer signal is the second voltage based on a voltage supplied by the first voltage source.

10. The image sensor according to claim 1, wherein:
each of the plurality of pixels has a switching unit that electrically connect or disconnect the supply unit and the first voltage source.

11. An electronic camera comprising the image sensor according to claim 1.

* * * * *